United States Patent
Patron (10) Patent No.: US 8,545,423 B2
(45) Date of Patent: Oct. 1, 2013

(54) CUSTOM FIT CERVICAL COLLAR

(76) Inventor: Martin Rizo Patron, Carpinteria, CA (US)

(*) Notice: Subject to any disclaimer, the term of this patent is extended or adjusted under 35 U.S.C. 154(b) by 900 days.

(21) Appl. No.: 12/227,757

(22) PCT Filed: Aug. 11, 2006

(86) PCT No.: PCT/US2006/043840
§ 371 (c)(1),
(2), (4) Date: Nov. 25, 2008

(87) PCT Pub. No.: WO2008/057095
PCT Pub. Date: May 15, 2008

(65) Prior Publication Data
US 2009/0247918 A1 Oct. 1, 2009

(51) Int. Cl.
*A61F 5/00* (2006.01)
(52) U.S. Cl.
USPC ...................................... 602/18; 128/DIG. 23
(58) Field of Classification Search
USPC .................. 602/5, 18, 17, 517; 128/DIG. 23; D24/191
See application file for complete search history.

(56) References Cited

U.S. PATENT DOCUMENTS

| | | | | |
|---|---|---|---|---|
| 2,828,736 A | * | 4/1958 | Monfardini | 602/18 |
| 3,042,027 A | * | 7/1962 | Monfardini | 602/18 |
| 3,188,605 A | * | 6/1965 | Slenker | 439/750 |
| 5,056,508 A | * | 10/1991 | Brunell | 602/18 |
| 5,215,517 A | * | 6/1993 | Stevenson et al. | 602/18 |
| 5,230,698 A | * | 7/1993 | Garth | 602/18 |
| 7,041,073 B1 | * | 5/2006 | Patron | 602/17 |

* cited by examiner

*Primary Examiner* — Kim M Lewis
(74) *Attorney, Agent, or Firm* — Mark Rodgers

(57) ABSTRACT

An improved cervical collar suitable for use in emergency or non-emergency situations for adjustment on or off a patient including the elements of an ergonomic occipital support region 102, a bridge junction 119 and an ergonomic spinal support region 101, an adjustable height neck support region 103, the neck support region is vertically aligned but may be horizontally offset, the spinal support region is stoppably and stowably hinged with the occipital support region at the bridge junction, the occipital support region is independently circumferentially sized and positioned adjustably with the neck support region; the spinal support region is independently and adjustably secured to the neck support region distinctively from the occipital and neck support region connections.

4 Claims, 7 Drawing Sheets

CUSTOM FIT CERVICAL COLLAR

RELATED DOCUMENTS

None

FIELD OF THE INVENTION

The present invention is in the area of cervical collars, and more particularly improved cervical collar suitable for use in emergency situations that can be stored flat or substantially flat, which substantially immobilizes the head and neck regions of a person in relation to the thorax.

BACKGROUND OF THE INVENTION

As per standard emergency protocols, first responders such as firefighters and paramedics must allocate at least one person to initiate cervical spine immobilization protocol for a trauma or accident victim with suspected head, neck or spinal injuries. The reason for this is in part to immobilize the victim's head to prevent or at least mitigate further injury to the neck region and/or spinal column. If the victim moves their neck or head in any direction, serious and debilitating injuries may ensue.

Currently, there is no cervical collar suitable for use in emergency situations which sufficiently immobilizes the head, neck and spinal regions of such a victim. In fact, if one were to put on any existing cervical collar, one would find that there is very limited restriction as to the movement of one's head and neck regions in relation to thorax. While existing cervical collars do offer some support for trauma victims they do not completely immobilize the victim. In fact, a person fitted with an existing cervical collar can move their head up, down, and sideways with a significant range of motion. In particular, the neck region will move in respect to the thoracic cavity and may exacerbate existing injuries.

This deficiency is manifested most fully when an accident victim is to be transferred on to a backboard. An existing cervical collar will simply not sufficiently restrict movement of neck regions in relation to the thorax so that an aid rescuer may move the victim in a safe way. And because existing cervical collars do not restrict movement, a first responder cannot leave a collared victim unattended, so a single responder is incapable of initiating spinal stabilization upon a multiple number of victims.

Another troublesome deficiency of today's cervical collars is that there is no way to safely adjust the neck size of victim's collar after the cervical collar is placed on victim while still also maintaining access to the trachea area of the victim. Currently, the art allows on-victim adjustment only while blocking access through the collar to the trachea area, as taught by Koledin in U.S. Pat. No. 6,423,020. Such access is critical to address incidences where an accident victim has potential both for a spinal cord injury and for advanced airway procedures at the same time.

All other collars in the art, such as those taught by Martin in U.S. Pat. No. 5,520,619 and Rudy in U.S. Pat. No. 5,593,382, must be adjusted prior to being put on a victim because the collar lacks immobilization capability and features that allow aid rescuers to avoid the potential of hyper-extending a victim's neck when adjusting it in place. In these cases a rescuer must make a rough estimate as to which size a victim's neck is and hope their guess reasonably approximates victim's neck size in order to adjust the neck brace before putting it on the patient. If rescuer's guess is not close, rescuer either must take off the cervical collar or leave the cervical collar on and hope that injuries to victim are not thereby exacerbated. Moreover, oftentimes, in the heat of the moment in an emergency an aid rescuer does not have enough time to properly size up victim's neck.

Furthermore, rescuers are trained to immobilize the cervical area of a trauma victim, who may be in any number of positions at the time, in what is called a neutral position. This is the position of the head, neck and spine in the manner in which they appear with a human body lying supine with palms facing upward. With this alignment, the potential for injuries to these areas is decreased. However, no cervical collar used today for emergency situations can be adjusted after placing it upon a victim in such a way as to securely immobilize the victim in a preferred position.

Existing one-piece collars designed for use in emergency medical situations such as those taught by Koledin in U.S. Pat. No. 6,423,020, Garth in U.S. Pat. No. 4,413,619, Martin in U.S. Pat. No. 5,520,619, and Rudy in U.S. Pat. No. RE36745 are designed to match their symmetrical neutral position to a default body type and size. As a result, they allow for only one lateral, or side-to-side default position of immobility and are unable to align symmetrically for different sizes and body types of patients. As a result, rescuers using existing collars are unable to immobilize many victims' heads in a perfect neutral alignment.

In addition, in many cases as a result of their circumstances, victims may experience severe pain to move from a non-neutral position in order for a collar to be put on. These victims need to be immobilized as such in their position of comfort. However no collar exists for use in emergency medical situations that can fill this need. Application of existing collars to these victims causes unnecessary pain and discomfort, as responders are forced to move the victim's head away from a position of comfort to the default position of the collar.

Existing collars with two or more pieces for the occipital support and neck support regions such as those taught by Stevenson in U.S. Pat. No. 5,215,517 and Schmid in U.S. Pat. No. 5,058,572 have only one strap of some sort holding the two regions together to form the collar. As such they are better suited to maintain symmetry for a neutral position across a limited range of physical body types and sizes than the one-piece collar types. However, this art misses two critical elements that exist nowhere prior to the present invention. They are not capable of simultaneously allowing a broad range of relative placement of the two regions in both right and left directions as required to maintain neutral symmetry while at the same time allowing circumferential adjustment to accommodate a range of body sizes. Moreover, existing two-piece collars do not enable the two regions to be secured such that the victim may be immobilized in a specific, intentionally non-neutral position. This is because these devices have only one strap and as such are not able to independently adjust the length of the strap on both sides of the collar at the same time, and because they have no means of securing those straps independently relative to each of the two regions of the collar.

In addition, state of the art cervical collars used for emergency situations have several requirements that other collars typically used in hospital or home based medical care situations do not. They must be able to be stored flat for efficient storage inside emergency vehicles and they must be relatively fast and easy to use. They must be inexpensive as they are typically one-time use devices. They must also be made of non-metallic materials that are transparent or translucent to medical X-ray.

Other cervical immobilization devices with far more components, complexity and cost have some means to immobilize a person's cervical spine in a non-neutral position. Such collars as those taught by Lerman in U.S. Pat. No. 6,267,741 and Grober in U.S. Pat. No. 6,045,522 are very complex traction apparatus, with multiple pieces added to the collar such as front chest, back, and shoulder supporting members and multiple, adjustable, metallic connection means. These types of collars are designed for care center or home use and are simply not suitable for emergency situations, as they do not meet the needs for fast and easy application, low cost, flat storage, and X-ray compatibility.

Therefore, what is clearly needed in the art is an improved cervical collar suitable for emergency medical situations that will better immobilize a victim's head and neck relative to their thoracic regions. In addition, an improved collar will immobilize a victim in the position most suited for the circumstances whether a neutral position or a non-neutral position of comfort. It is necessary to develop such a cervical collar which offers substantial support to the regions in its chosen position. Furthermore, the emergency medical field is in need of a cervical collar that is designed to be custom fitted to the patient's physique, in a diversity of sizes and positions simultaneously to accommodate a variety of incidents or needs, after it is placed around the patient's neck. The current art does not offer a device with such capabilities which is also especially designed for extrication and rescue operations.

SUMMARY OF THE INVENTION

The invention is an improved cervical collar suitable for use in emergency or non-emergency situations for adjustment on or off a patient including a spinal support region, an occipital support region, a bridge junction, and an adjustable height neck support region; the spinal support region is independently and adjustably connected diagonally to opposite sides of the neck support region using at least two fastening straps, which when secured in said cross-tensioning manner results in a substantially tighter and more form-fitting collar, and which when arranged into an ergonomically and suitably designed collar result in substantially more immobilization to the wearer's head and neck; the cervical collar has at least two anchoring straps connecting the occipital support region with the neck support region, distinct from the spinal and neck support region fastening strap connections, for simultaneous and independent adjustment of both circumferential size and positioning, resulting in the capability to immobilize a patient of very large or very small size in a perfect neutral position facing forward or in a non-neutral position of comfort where the patient's head may be facing toward the direction of one shoulder; the neck support height may be adjusted while remaining vertically aligned but may be intentionally horizontally offset, resulting in different heights on either side of the neck support region to accommodate the fit requirements of a victim whose head is immobilized in a direction facing towards one shoulder, with correspondingly distinct distances from the left and right sides of the head to his sternum; the spinal support region is stoppably and stowably hinged with the occipital support region at the bridge junction.

In some embodiments, the neck support region height is adjusted with a dual adjustment system including locking tabs, locking teeth, and adjusting tabs, with additional mating features on the two members of the neck support region to assure vertical alignment but also to allow horizontal offset, or different heights for left and right sides of the neck support region. In some embodiments, adjustment system also includes a ratcheting means such that the vertical height of the neck support region on each side may be adjusted only in an opening or increasing height direction unless the ratcheting mechanism is released. In some embodiments, the neck support region includes a mandible support and/or a chin strap. In some embodiments, the occipital and neck support regions include means such as mating guides and tracks to keep said regions aligned and concentric during application of the collar to a patient. In some embodiments, neck support regions include indices for visual confirmation and control of neck support vertical height, horizontal alignment, and positioning. In some embodiments, occipital and spinal support regions include indices for visual confirmation and control of circumferential sizing, alignment and positioning. In some embodiments, dual adjustment system on neck support region includes features such as suitably positioned tabs for adjustment of neck support height while collar is on patient such that no forces are exerted on patient.

In some embodiments, portions of the collar inner region comprises foam padding material affixed to a plastic material outer region. In some embodiments, the cervical collar occipital arid/or spinal support regions are ergonomically designed to approximate the natural shape of a human body. In some embodiments, the anchoring and/or fastening straps are enabled by cooperating hooks and loops material. In some embodiments, the spinal or occipital support region includes means to hold and stow fastening straps in ready position until used.

DESCRIPTION OF PREFERRED EMBODIMENTS

According to a preferred embodiment of the present invention, an article of manufacture is used for the immobilization of the cervical region of an injury victim by rescuers. The article of manufacture will be explained in enabling detail below.

It should be noted here some terms which will be used hereafter. The terms "patient" and "victim" refer to the person upon which the cervical collar is fitted. Although the word "victim" typically connotes someone who has befallen a crime or a serious accident, the present invention may be used in circumstances where there has not been a serious accident or a crime.

Figure 1:
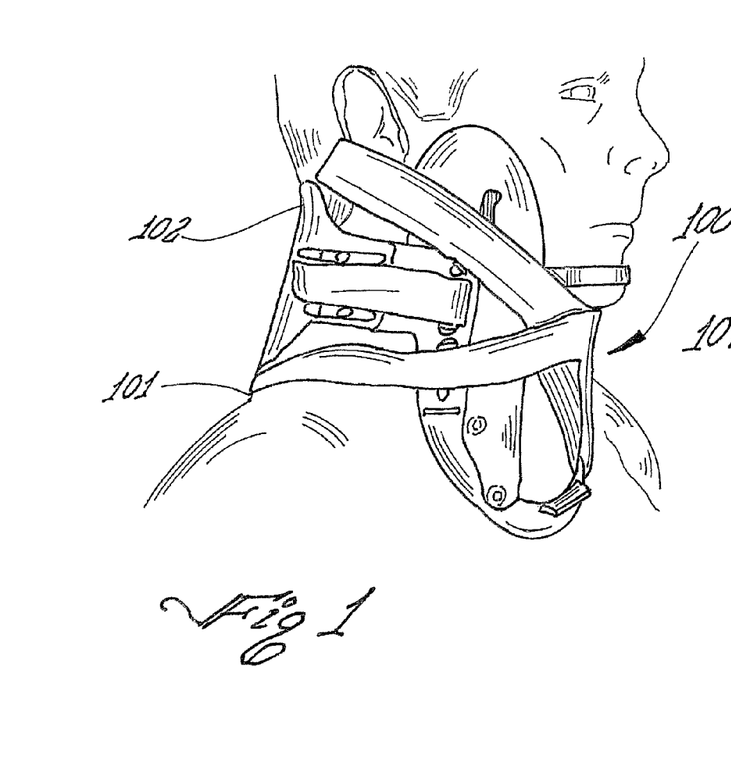
FIG. 1 is a perspective view of the preferred embodiment of the present invention.
Figure 2:
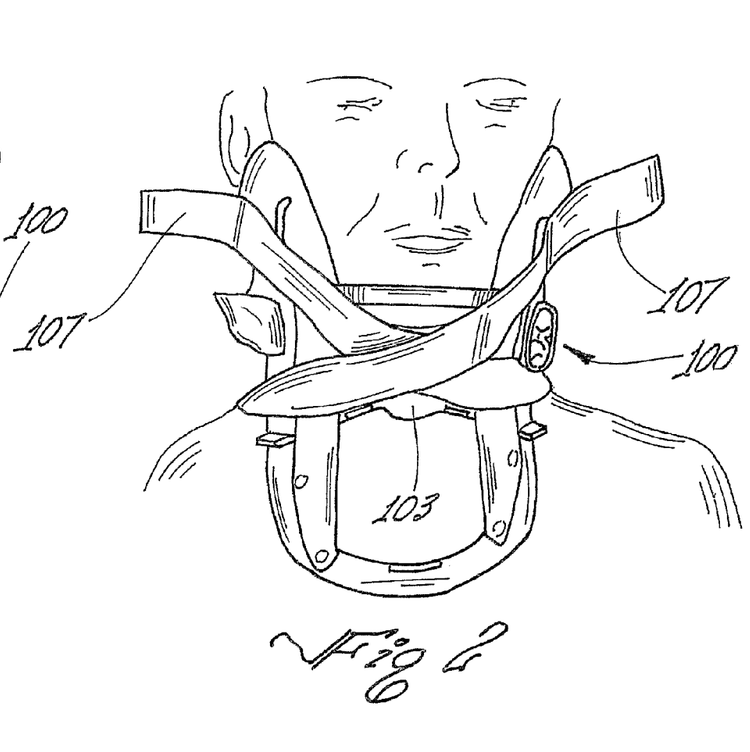
FIG. 2 is another perspective view of the preferred embodiment of the present invention.

FIGS. 1 and 2 are perspective views of the preferred embodiment of the present invention. The present invention can be described as having three discernable regions. The preferred embodiment includes a spinal support region 101, an occipital support region 102 and a neck support region 103. Notwithstanding the fact there are three discernable regions, it is understood that the present invention is not necessarily an assemblage of three different parts.

As shown in these figures, there is a fastening strap 107 originating from each side of spinal support region 101. These straps cross each other in front of the victim's neck and attach to the opposite side of neck support region 103. The straps are fastened in this crossing manner after the cervical collar is placed around the victim's neck. Cervical collar 100 is preferably composed of a flexible plastic sheet material or injected plastic material. However, other materials may also be used to compose the cervical collar 100. For instance, in some embodiments, the cervical collar 100 may be composed of a transparent material. The particular transparent material may be plastic or any other suitable material which is pliable enough to bend for the purposes of the present invention. One reason a transparent material may be used is for a doctor to observe if there are any contusions, morphological anomalies of the neck, bleeding, injuries, or anything else which may prove instructive for the purpose of treating the victim. However, the use of transparent material or any other material is not specifically required to practice the present invention. Therefore, the use of transparent material should not be construed to limit the scope of the claims below.

Figures 3, 4, 5:
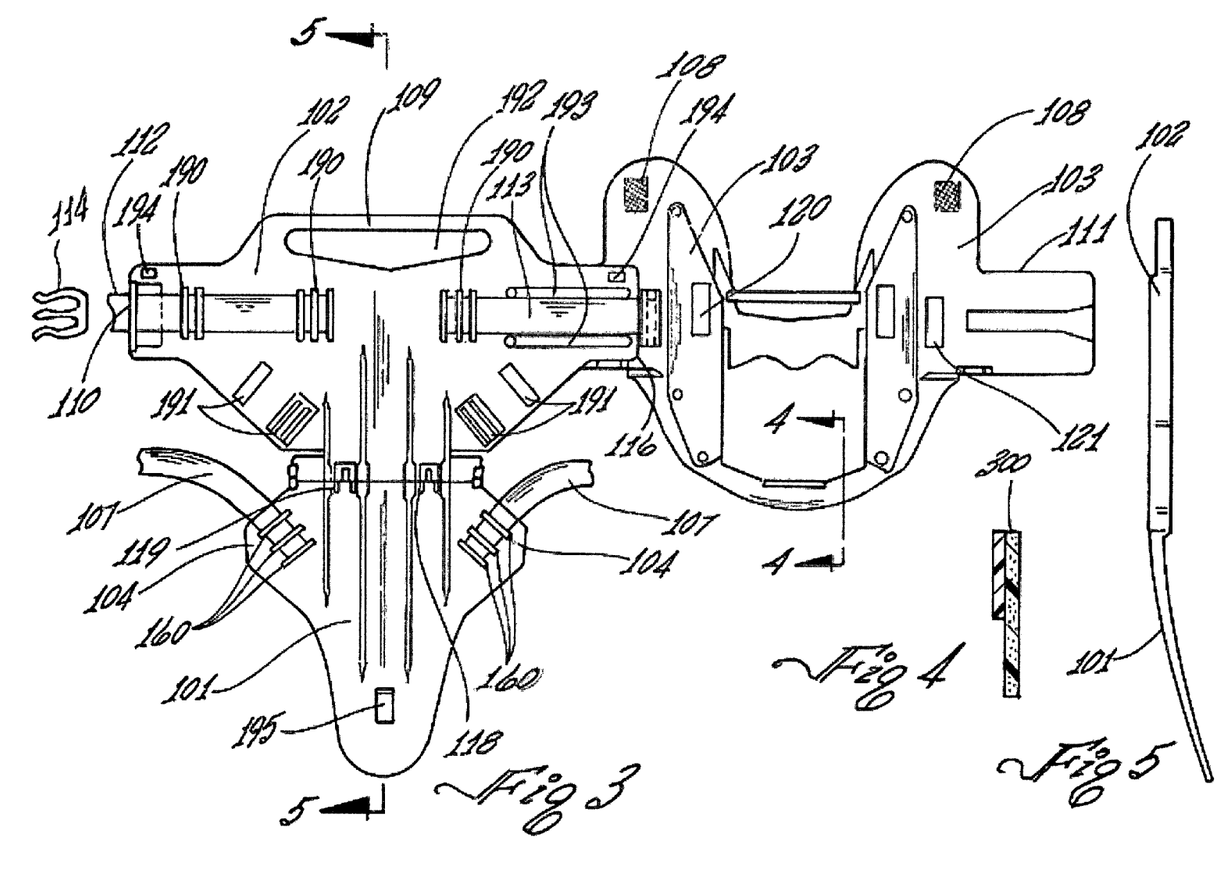
FIG. 3 is a plan view of the preferred embodiment of the present invention.
FIG. 4 is a cross-sectional view of the preferred embodiment of the present invention.
FIG. 5 is a cross-sectional view of the preferred embodiment of the present invention.

FIG. 3 is a perspective view of the preferred embodiment of the present invention. The cervical collar 100 is normally flat as seen in FIG. 3, and has sufficient length and flexibility to encircle a victim's neck in use.

It should be pointed out here that there are fundamental differences between the present invention and the prior art. Unlike the prior art where there is only either one way to adjust the size of the circumference of the collar to fit around a patient's neck, or one way to adjust the position of the collar at a given circumference, the present invention enables a person to adjust both its circumferential size and its position simultaneously. This is a vast improvement in the art because this enables a rescuer to properly adjust the cervical collar in such a way to be secured preferentially off-center in how it is fitted or to be secured perfectly centered, regardless as to the circumferential size of a patient. Existing collars are either of a fixed circumference to enable them to be symmetrically centered on a patient, or they have adjustable circumferences which require them to become off-centered on a patient with any circumference other than the single default circumference of the collar.

For instance, if a victim's head or neck has been injured and his head is positioned in a direction facing towards his right shoulder, existing collars would require that the victim's head be turned to the left in order to be approximately centered such that the face is pointed directly forward. By moving the victim's head, this may cause further pain or injury and thereby exacerbate his injuries.

Figure 6:
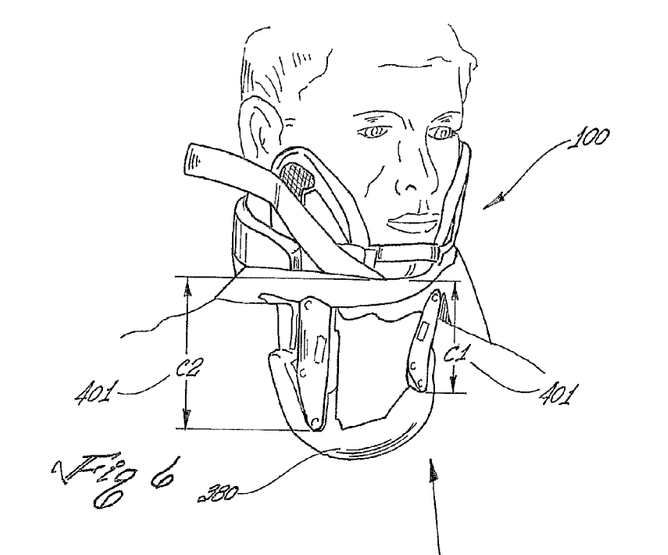
FIG. 6 is a perspective view of the preferred embodiment of the present invention.
Figures 6A, 6C:
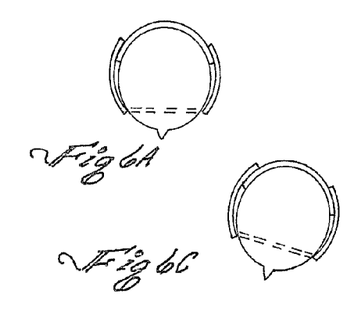
Figure 6B:
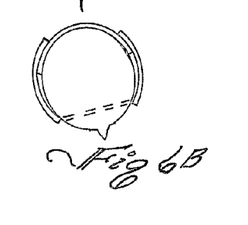

With the present invention, a dual independent lateral adjusting system enables a person to properly fit the cervical collar on the victim regardless of whether the head is positioned facing asymmetrically off-center, or symmetrically perfectly centered as desired. This is shown as follows: if the cervical spine is desired to be immobilized with the head in a position off center towards the direction of the left shoulder, it would look as shown in FIGS. 6 and 6b. Similarly, immobilization is shown with the head towards the right shoulder in FIG. 6c, and with the head facing forward in FIG. 6a. Further, unlike the prior art in which adjustable neck supports maintain horizontal alignment, the present invention provides a means to asymmetrically adjust the height of the neck support region to complement and properly fit with a patient whose head is immobilized in a direction off-center, facing in the direction of one or the other shoulder. In this way the cervical collar is designed to provide superior immobilization while maintaining a patient's position of comfort. The details of the preferred embodiment that enable this critical feature are described below.

Referring back to FIG. 3, spinal support region 101 is located below and adjacent to occipital support region 102. Connected with the occipital support region 102 is the neck support region 103. In addition, for purposes of clarification, "outer region" shall hereinafter refer to the side that faces outside. And "inner region" shall hereinafter refer to the side that comes into contact with victim's skin. FIG. 4 shows a cross-section view of inner region to which is affixed a padding material 300 for patient's comfort. Although in this preferred embodiment a foam material is used, it is not specifically required that all embodiments incorporate a layer of foam. In addition, other materials may be used for padding. In some preferred embodiments the foam may be placed and affixed to the inside region in any or every location where the collar presses against the victim's body when used. The use of foam is not to be construed to be limiting to the scope of the present invention.

Spinal support region 101 includes side regions 104 which preferably extend in a protruding manner oppositely from spinal support region 101. In other embodiments side regions 104 may be integral and not extending from spinal support region. Affixed to spinal support 101 are fastening straps 107. In the preferred embodiment each of the side regions 104 function as anchoring locations for at least one each fastening strap 107 for a total of at least two fastening straps.

In the preferred embodiment at least two fastening straps 107 are affixed to the spinal support region through the use of at least one window 160 on each side region 104 whereby the fastening strap is looped through the window or windows and secured back to itself. Other ways of attaching the fastening straps 107 to the spinal support region 101 may be used, such as buckles, slips, pins, rivets, or other attachment devices. In the preferred embodiment the inside and outside faces of fastening straps 107 may be enabled by VELCRO® (a trademarked material). These faces comprise both hooks material and inner loops material for the purpose of being detachably secured to each other.

Unlike the prior art, the present invention incorporates fastening straps 107 that connect the spinal support and neck support regions diagonally from opposite sides such that they provide tension, or a pulling type of force, from the upper part of one side of the neck support region to the other side of the spinal support region. To accomplish this in the preferred embodiment the fastening straps are long enough to wrap over the shoulder and around the neck of the victim as shown in FIG. 2 to cross each other in front of the neck and clasp onto cooperating hooks 108 situated on opposite sides of the neck support region 103. In this embodiment the fastening straps 107 are used to conjoin with cooperating hooks 108.

Fastening straps 107 are used as cross-tensioning structural members to create an interference, or tight fit of cervical collar 100 in relation to head, neck and thorax regions of body. This serves both to more closely fit the collar to the victim's particular morphology and to provide specific, key areas of ergonomic support for substantially improved immobilization capability. The novel strap arrangement acts in such a way, that when the straps are pulled and secured they provide the necessary leverage for improved fitting, tightness and support of the collar to the neck. This way, the present invention is substantially more stable and therefore provides substantially more immobilization than the prior art.

In other embodiments the fastening straps may be affixed to the neck support region and conjoined to the spinal support region such that the straps are pulled over the shoulder and around the neck in such a way that they cross each other in the area of either the occipital or spinal support region. It should be noted that the fastening straps may be arranged in any number of ways as long as one end of at least one first fastening strap is affixed to either the neck support region or the spinal support region, with the other end of the fastening strap made to forcibly pull on the other of the neck support region or spinal support region on the opposite side, and at least one other second fastening strap is arranged symmetrically about the collar with the first one. In the preferred embodiment this is done by such means as one fastening strap crossing one other fastening strap in front of the neck region.

In other embodiments, other methods of attaching the ends of fastening straps 107 to neck support region 103 or to spinal support region 101 may be used, such as buckles, clips, pins, or rivets, as long as at least one end of each fastening strap 107 is not permanently attached and as long as each fastening strap may be securely fastened with a variety of possible lengths such as to provide the means of forcibly pulling the two opposing regions together in a tightening direction. In other embodiments the fastening straps may attach in such a way that they provide cross-tensioning forces between the two regions without the straps physically crossing each other. For this reason, the scope of the present invention should not be construed to be limited only to a particular means of fastening strap material or attachment.

Figure 7:
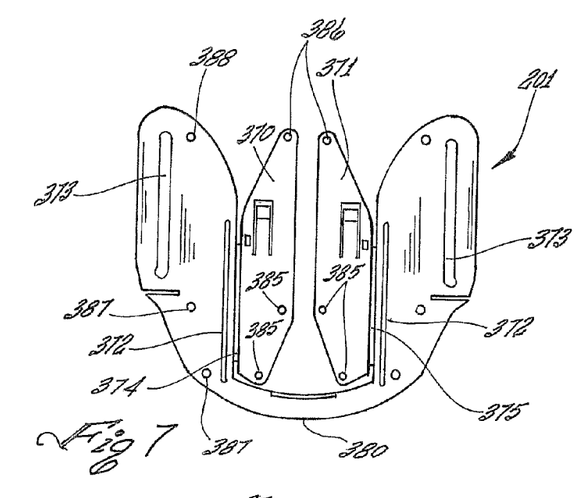
FIG. 7 is a plan view of the lower member of the neck support region in unassembled configuration.
Figure 9:
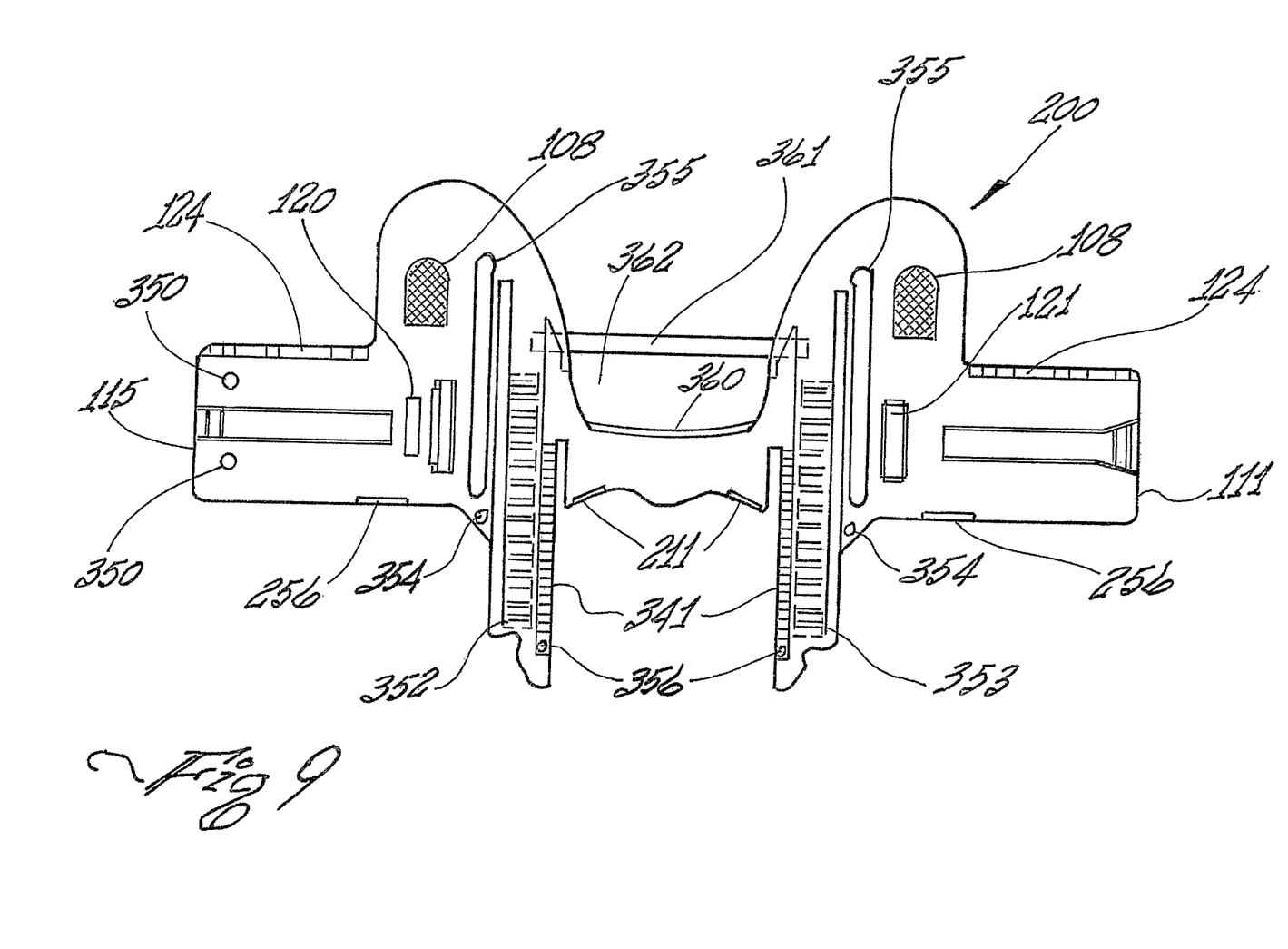
FIG. 9 is a plan view of the upper member of the neck support region.

Returning to FIG. 3, occipital support region 102 comprises upper edge 109, side edge 110 and side edge 116. Neck support region 103 comprises upper member 200 and lower member 201 (FIG. 7). Upper member 200 is sized to fit with lower member 201. As shown in FIG. 9, upper member 200 comprises side edge 111 and side edge 115, anchoring window 120 near side edge 115 and buckle clip 121 near side edge 111. Looking again to FIG. 3, anchoring strap 112 is affixed at side edge 110 of the neck support region and anchoring strap 113 is affixed at side edge 116. In the preferred embodiment, the anchoring straps 112 and 113 are Velcro® enabled, but in other embodiments they may be made of other materials. In the preferred embodiment, each anchoring strap is affixed with the occipital support region through use of vertical windows 190 on each side of the occipital support region, by means of looping through the windows and securing back to itself as a means of attachment and engagement. Moreover, it should be noted here that in other preferred embodiments the anchoring strap may be made of a different material and affixed to the occipital support by other devices such as buckles, pins, rivets, or other expedient means.

Anchoring straps 112 and 113 are each made to be adjustable in length to conjoin with neck support region 103 respectively at side edges 111 and 115, such that when the combined assembly is encircled about a victim's head and neck, each of the occipital support region and the neck support region may be independently positioned relative to one another after being placed upon the victim with the victim's head facing in a preferred direction before being secured tightly for immobilization of the victim's cervical spine area.

Referring to FIG. 3, in the preferred embodiment buckle 114 is attached to anchoring strap 112 for the means of conjoining securely with the neck support region with an adjustable strap length. Buckle 114 engages with buckle clip 121 situated near side edge 111 of neck support region 103.

In the preferred embodiment, anchoring window 120 is situated in neck support region 103 near side edge 115. Anchoring strap 113 is used to conjoin occipital support region at side edge 116 with variable length to neck support region at side edge 115 by means of looping through window 120 and securing back to itself by engaging and attaching the hooks and loops material of the strap. Other ways may be used to secure the strap back to itself as well, such as rivets or sewing.

In other embodiments, anchoring straps 112 and 113 may use other means of conjoining the occipital support region with the neck support region such that either end of each strap may be affixed to one region with the other end conjoining with the other region such that the length of each anchoring strap is independently adjustable and may be securely fastened. For this reason, the scope of the present invention should not be construed to be limited only to a particular implementation of anchoring strap attachment. The resulting arrangement allows the collar to immobilize the head and neck of a victim in either a symmetrical and aligned neutral position as shown in FIG. 6a, or an asymmetrical, non-neutral position of comfort as shown in FIGS. 6b and 6c.

Returning to FIG. 3, connecting spinal support region 101 and occipital support region 102 is bridge junction 119. In some preferred embodiments, the spinal support region is connected with the occipital support region at the bridge junction as one continuous piece. In this preferred embodiment, the spinal support region is connected with the occipital support region at the bridge junction through use of one or more hinges which interconnect with each other, resembling that of the bridge member in U.S. Pat. No. 7,041,073. In addition, junction buckles 118 provide a means of locking the spinal and occipital support regions in the open, ergonomic position, so that they may not close unintentionally when being applied to a victim. Other ways of joining the two regions may also be used. For this reason, it is not specifically required that either of these specific attachments be used. As such, the particular implementation of interconnecting the two regions should not be construed as limiting to the present invention.

In some preferred embodiments the occipital support region 102 further incorporates storage brackets 191. Storage brackets 191 provide a means of conveniently storing or retaining the fastening straps so that they do not get in the way or become out of reach when the collar is slid behind a victim's back for application. In the preferred embodiment storage brackets are formed by protruding pieces of plastic which rise from the occipital support region. It should be noted here that storage brackets are not necessary in all embodiments of the present invention. Other preferred embodiments may forego this piece or may form the brackets with differing implementations. For this reason the scope of the present invention should not be construed to incorporate storage brackets in all embodiments.

In the preferred embodiment the occipital support region further incorporates a top window 192. Top window is used in order to ergonomically conform the occipital support region to the morphology of the head of a patient. Obviously, there abounds a vast array of different morphologies of peoples' heads; for example some are egg-shaped, some possess protrusions on their back sides, some heads are large, some are small, etc. The top window is ergonomically designed in order to make the occipital support more flexibly conform and comfortably fit with the backside of a person's head.

Also as shown in FIG. 3, clip 195 is located toward the bottom of spinal support region. Clip 195 may be affixed to spinal support region as a separate piece or integral with it. In some preferred embodiments clip 195 provides a means of stowing securely the spinal support region in a folded position, such that clip 195 engages occipital support region near upper edge 109. Other embodiments may forego this piece or may form the clip in another fashion.

In the preferred embodiment there are sliding windows 193 on occipital support region 102 as shown in FIG. 3, and mating attachment bosses 350 on neck support region 103 as shown in FIG. 9. Attachment bosses 350 are sized to fit inside and track along sliding windows 193 as the occipital and neck support regions are overlappingly engaged and circumferentially sliding relative to one another as cervical collar 100 is bent to encircle and size to a victim's neck. This engaging mechanism controls the outside diameter or circumference of the present invention in a controlled and aligned fashion such that the occipital and neck support regions remain supportively overlapping and concentric. In some preferred embodiments these features may be of different designs as long as they geometrically mate with each other to perform the desired function.

In the preferred embodiment there may be index windows 194 near side edges 110 and 116 of occipital support region 102 as shown in FIG. 3 and index scales 124 near side edges 111 and 115 of neck support region 103 as shown in FIG. 9. Index windows and index scales are located such that in the assembled condition the index scales are visible through the index windows so as to allow visual indication of adjustment length on each side of cervical collar. In this manner by preference of a rescuer, a perfect neutral position may be obtained for any size circumference by alignment of equal index scale indices on each side, or an intended position of comfort may be confirmed and substantiated with identification of resultant relative positions. In other embodiments, alternate implementations may fulfill the purpose of visual identification of relative positioning from side to side such as tabs, pins, or other markers with corresponding mating features on occipital and neck support regions, and as such the scope of the present invention should not be construed to incorporate index windows and scales in all embodiments nor should it be limited to this method of identification of relative size and positioning of each side of the collar.

Unlike the prior art as in U.S. Pat. No. 7,041,073, by the same inventor, the spinal support region 101 may preferably be ergonomically shaped as shown in FIG. 5 to provide anatomical support with the morphology of a patient's natural curvature of spine (or bent in a manner towards the natural curvature of a victim's back when worn). The ergonomic shape of spinal support region 101 in conjunction with the fastening straps will support a victim's head in its natural upright position thereby avoiding hyper-extension of the neck and exacerbating any potential pre-existing injuries. The ergonomic configuration also facilitates easier sliding of the present invention under a victim lying on the ground facing up or seated firmly in their car with their back in contact with the surfaces behind them, because there will be less surface area in contact between the collar and those elements. This bend may preferably be formed directly in the cervical collar shape simply using molded materials such as injection molded plastic. Or in some embodiments similar to U.S. Pat. No. 7,041, 073 the bend may be formed by holding the spinal support region at an angle by means of a junction.

As shown in FIG. 9, upper member 200 also comprises flanges 352 and 353, vertical windows 355, top edge 360, chin strap 361, shelf strap tabs 211, and push tabs 256. Chin strap 361 is affixed to upper member such that it forms window 362 above top edge 360. In the preferred embodiment chin strap is Velcro® enabled and is positioned and is adjustable in length such that it wraps around the front of a victim's chin when the cervical collar encircles the victim's neck. Chin strap is provided to accommodate victims of smaller or thinner head shapes or sizes, for use with or without other means of mandible support, such that the cervical collar circumference is prevented from becoming smaller and the neck support region is held at a minimum distance from the victim's neck as the collar is tightened. Chin strap also provides additional structural stability to the collar by providing another connecting link between the somewhat flexible left and right sides of the neck support region. Although in this preferred embodiment Velcro® material is used, it is not specifically required that all embodiments incorporate Velcro® as the material for the chin strap. Further, it should be noted here that chin strap is not necessary in all embodiments of the present invention. Other embodiments may forego this piece or may form the chin strap in another way. For this reason, the use of a chin strap or the use of Velcro® for the chin strap is not to be construed to be limiting to the scope of the present invention.

Figure 8:
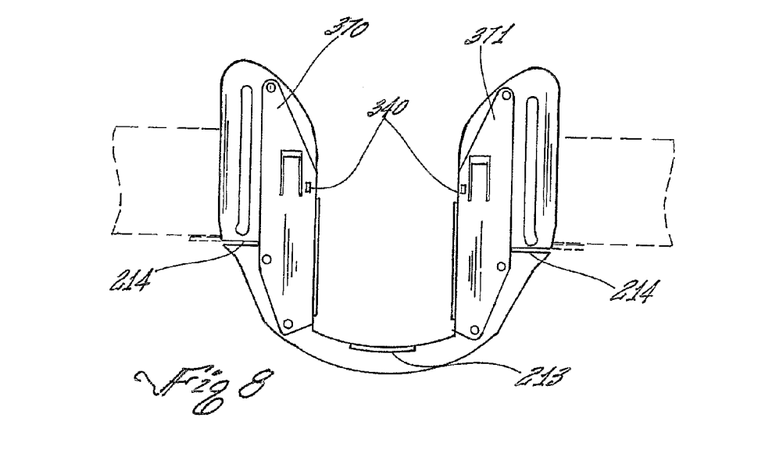
FIG. 8 is a plan view of the lower member of the neck support region in use configuration.

As shown in FIGS. 7 and 8, in the preferred embodiment lower member 201 is comprised of wings 370 and 371, lower windows 372, upper windows 373, junctions 374 and 375, lower edge 380, mount pins 385, guide pins 386, pull tabs 214, and sternum tab 213. Wings 370 and 371 are enabled to fold about junctions 374 and 375, respectively, such that the wings flip 180 degrees out and enable mount pins 385 and guide pins 386 to engage securely with pin holes 387 and 388, respectively, holding the wings at a fixed distance from and creating a gap with the lower member. In this manner, junctions 374 and 375 each form a channel shape in which flanges 352 and 353 respectively, of upper member 200, slideably and snugly but somewhat flexibly engage, to enable the lower member and the upper member to move up and down relative to one another and be positioned in order to custom fit with the neck length of a victim.

Wings 370 and 371 are folded in such a manner and positioning with upper member 200 as to capture the flanges within the formed said channels. FIG. 8 illustrates lower member 201 with wings folded in place without showing upper member for visual clarity. In other embodiments, wings 370 and 371 may be separate pieces and assembled separately rather than one continuous piece connected in a foldable fashion with lower member 201. It should also be noted that other implementations of connecting the wings with the lower member may be used rather than guide pins, mount pins and associated pin holes. Such devices may include rivets, spacers, bushings, molded-in features and in position or in any combination thereof. As such, the scope of the present invention should not be construed to incorporate one-piece lower members or pins and pin holes in all embodiments.

In the preferred embodiment, plastic rivets 354 are affixed to upper member 200 (shown in FIG. 9) such that they slideably engage with and track within upper windows 373 in lower member 201. When assembled in this manner, guide pins 386 in lower member 201 slideably engage with and track within vertical windows 355 in upper member 200, and button tabs 356 in upper member 200 slideably engage with and track within lower windows 372 in lower member 201. With the rivets, pins and button tabs thus captured, engaged and tracking in each other's respective vertical windows, the upper and lower members thus maintain vertical alignment and are limited in the extent to which they can move relative to one another.

Note however that unlike the prior art such as that taught by Martin in U.S. Pat. No. 5,520,619 and Rudy in U.S. Pat. No. RE36745, the present invention is not limited to maintaining horizontal alignment of the neck support region or its means of mandible support. Rather, the intra-member vertical window tracking and alignment system described above may be used with the use of somewhat flexibly designed members or material such that either side may be offset in vertical height relative to the other as illustrated in FIG. 6. This capability for offset horizontal alignment of the neck support region is complementary with the ability of the collar to immobilize a victim in a non-neutral position of comfort. When the collar is secured in a preferred position of comfort with the head facing toward one shoulder as in FIG. 6 rather than directly forward, the near height 401(c1) from the victim's jaw to his sternum at lower edge 380 is shorter than the far height 401(c2) on the other side of his jaw. To accommodate these different distances at varying angles of preferred positions of comfort, the neck support region may be thus intentionally horizontally offset in height with one distance longer than the other. In addition, upper member 200 and lower member 201 may be configured with varying stiffness such that top edge 360 stays substantially horizontal, with the difference in vertical lengths thus being applied only in a downward direction toward lower edge 380. In this way, while turned in a direction toward one shoulder the victim's head remains substantially level, while the collar adjusts in form only at lower edge 380 such as to conform with the offsetting distance from either side of their neck to their sternum.

In the preferred embodiment there may be scale windows 340 one each per wings 370 and 371 of lower member 201 as shown in FIG. 8 and index scales 341 one each per flange 352 and 353 of upper member 200 as shown in FIG. 9. Scale windows and index scales are located such that in the assembled condition the index scales are visible through the scale windows so as to allow visual indication of adjustment height on each side of neck support region. In this manner by preference of a rescuer, a perfect horizontal alignment position may be obtained by alignment of equal index scale indices on each side, or an intended offset vertical height position may be confirmed and substantiated with identification of resultant relative positions. In other embodiments, other devices may fulfill the purpose of visual identification of relative positioning from side to side such as tabs, pins, or other markers with corresponding mating features on upper and lower members, and as such the scope of the present invention should not be construed to incorporate windows and index scales in all embodiments nor should it be limited to this method of identification of relative positioning of each side of the neck support region.

Figures 10, 11, 12:
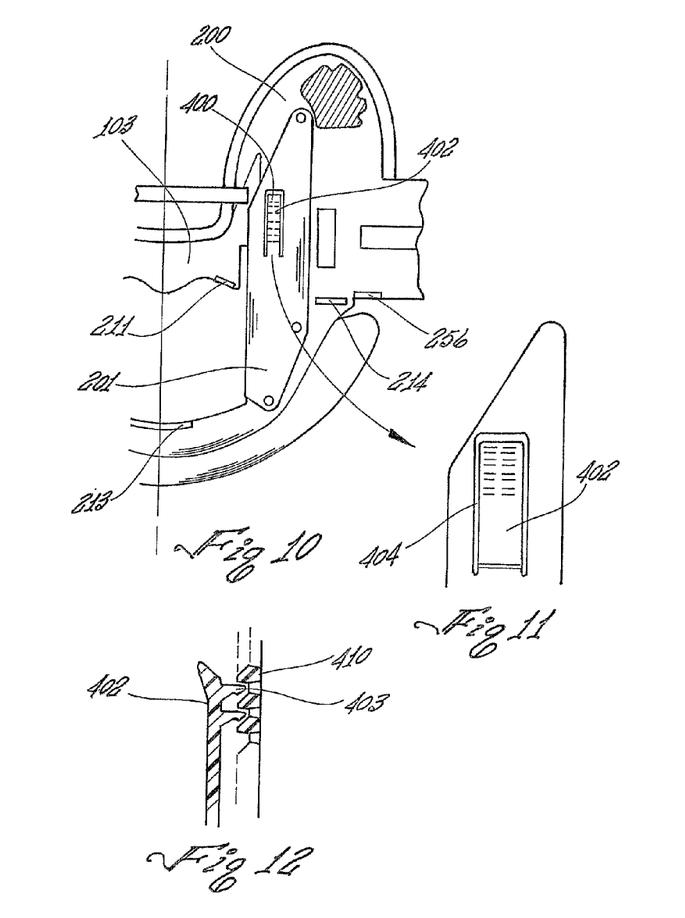
FIG. 10 is a detailed view of the neck support region adjustment system.
FIG. 11 is a detailed view of a part of the neck support region.
FIG. 12 is another detailed view of the neck support region.

FIGS. 10 through 12 illustrate a dual tab self-locking adjustment system 400 (hereafter DAS 400). DAS 400 is located on opposite sides of neck support region 103, one side of which is shown in FIG. 10. DAS 400 is made for adjusting and securing near and far heights 401(c1) and 401(c2) independently to the make the height of neck support region the same as the length of a victim's neck such that it fits him securely regardless of the preferred position of immobilization.

Most of the prior art does not provide a way to adjust a cervical collar for the length of a victim's neck after the cervical collar is placed upon the victim. The DAS system provides for the ability to adjust the neck size for a patient after placement. This ensures the best fit and provides for better immobilization.

DAS 400 comprises pull tabs 214, clavicle tab 213, strap shelf tabs 211 and push tabs 256 (shown in FIG. 10), locking tabs 402, locking teeth 403 and female members 410 (shown in FIG. 12), and windows 404 (see FIG. 11). Locking teeth 403 are made to engageably fit with female members 410. Locking tab 402 is connected with locking teeth 403 which directly engage with female members 410.

In the up position, or position in which the top of the upper member and bottom of lower member are closest to each other in an assembled condition, the lower member and upper member are allowed to move with respect to each other and thereby allow a user to find the correct neck size for a victim. In order to operate DAS 400, a rescuer uses both hands to respectively and simultaneously push up on strap shelf tabs 211 or push tabs 256 and down on pull tabs 214 or clavicle tab 213. This increases the distance between the upper and lower members thereby increasing the height of the neck support region.

Locking tab 402 is flexibly affixed to lower member 201 such that locking teeth 403 forcibly rests against female members 410. In some preferred embodiments, locking teeth and female members are shaped in such a way as to provide a ratcheting function, such that they allow motion in only the opening, or increasing height direction. In this embodiment the teeth and female members may be shaped as substantially right triangles. In this embodiment said ratcheting function may be released by grasping locking tabs 402 and pulling them away from female members 410 while simultaneously pushing upper and lower members towards each other.

After lower member is moved sufficiently far enough to fit victim's neck size and position, lower and upper members are locked in relative position by pressing locking tabs 402 to engage locking teeth 403 with female members 410.

An additional purpose of the strap shelf tabs is to prevent the fastening strap from traversing the window which exposes the throat of a victim. With the use of the strap shelf tabs, the fastening straps are pulled over the tabs. The purpose of the clavicle tab is for providing another point whereby a rescuer can pull down the lower member in order to adjust for the length of a victim's neck. In addition, the clavicle tab provides stiffening to lower member at lower edge 380 where it interfaces with a victim's sternum, thereby flattening the lower member locally to be more aligned in parallel and thus more stable and comfortable with victim's chest.

Figure 13:
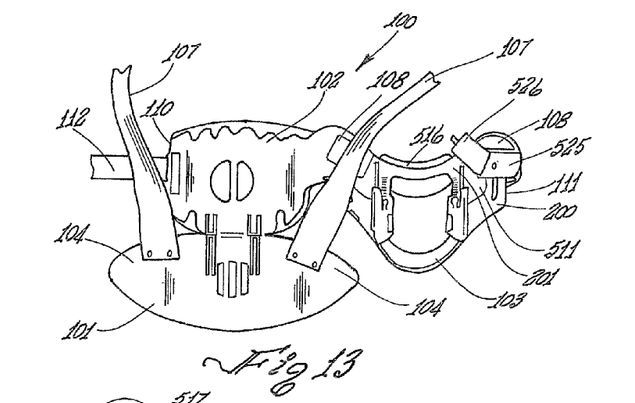
FIG. 13 is a plan view of another, non-preferred embodiment of the invention.
Figures 14, 15:
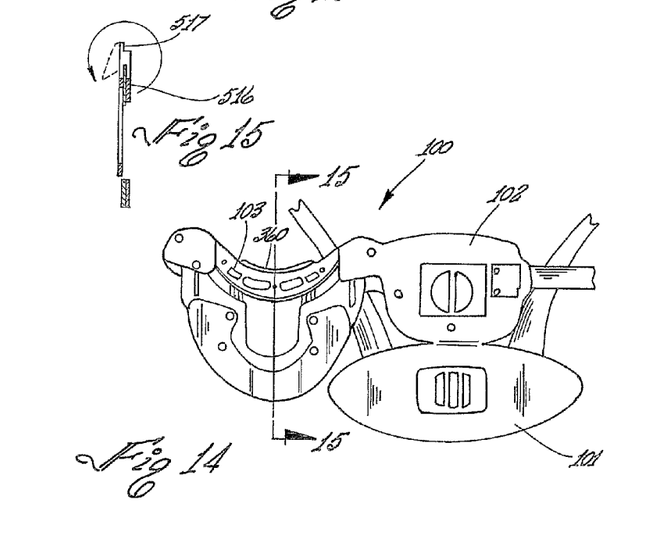
FIG. 14 is another plan view of a non-preferred embodiment of the invention.
FIG. 15 is a cross-sectional view of a non-preferred embodiment of the invention.

A non-preferred embodiment is shown in FIGS. 13 and 14. This embodiment does not provide all of the benefits of the preferred embodiment, but still is superior to the existing art. This embodiment is shown to illustrate that other embodiments which practice some of the novel features of the invention provide advantageous results. The alternative embodiment is also shown to illustrate that the exact shape of the parts of the collar are not specifically part of the novelty.

Situated on the inside of neck support region 103 is mandible support 516. FIG. 15 is a cross-sectional view showing a mandible support 516 affixed to top edge 360 via a hinging means 517. There may be two hinging means located on both sides of mandible support 516. It should be noted here that mandible support is not necessary in all embodiments of the present invention. Other embodiments may forego this piece or may form the mandible support in another fashion. For this reason the scope of the present invention should not be construed to incorporate mandible support in all embodiments.

Referring back to FIG. 13, situated on upper member 200 is again cooperating hook 108. An additional cooperating hook 525 is situated near side edge 111 for engagement with anchoring strap 112 instead of a buckle type attachment. Further, cooperating hook strap 526 is affixed to lower member 201 near side edge 511. In this embodiment anchoring strap 112 may be dual layered with cooperating hooks and loops. Cooperating hook strap 526 is thus used to provide additional means of support. After fastening strap 107 is placed upon cooperating hook 108, cooperating hook strap 526 is placed upon anchoring strap 112.

It will be apparent to the skilled artisan that there are numerous changes that may be made in embodiments described herein without departing from the spirit and scope of the invention. Other features not mentioned in the specification, but known to one skilled in the art may be integrated as well without departing from the spirit and scope of the present invention. There are, for example, a wide array of materials, apparatuses, and methods which may be interchangeably used there are many changes that may be made in dimensions and so forth to accommodate different needs which may be used, all within the scope of the invention. The methods, system, and apparatuses of the present invention should therefore be afforded the broadest possible scope under examination. As such, the invention taught herein by specific examples is limited only by the scope of the claims that follow.

I claim:

1. A cervical collar comprising:
a spinal support region;
a neck support region;
fastening straps connecting the spinal support and neck support regions diagonally from opposite sides of the cervical collar such that the straps provide cross-tensioning forces between the opposite sides of the spinal regions by forcibly pulling them together in a tightening direction or in a direction that increases the tightness of the collar on the person wearing it; and
strap shelf tabs located on the neck support region.

2. A cervical collar of sufficient length and flexibility to encircle a patient's neck, comprising:
a spinal support region;
an occipital support region;
a neck support region; and
two independent adjustable anchoring straps, one on each side of the cervical collar, connecting the occipital support region with the neck support region with sufficient adjustment capability for simultaneous and independent adjustment of circumference and positioning angle of patient's head relative to thorax;
wherein the spinal, occipital and neck support regions are formed from at least two subassemblies and the collar is essentially planar before installation on a victim, further comprising at least two fastening straps connecting the spinal support and neck support regions from opposite sides such that the straps provide cross-tensioning forces between the opposite sides of the spinal and neck support regions by forcibly pulling them together in a tightening direction or in a direction that increases the tightness of the collar on the person wearing it.

3. A cervical collar of sufficient length and flexibility to encircle a patient's neck, comprising: a spinal support region, an occipital support region, a neck support region, and; two independent adjustable anchoring straps one on each side of the cervical collar connecting the occipital support region with the neck support region with sufficient adjustment capability for simultaneous and independent adjustment of circumference and positioning angle of patient's head relative to thorax, wherein: the spinal, occipital and neck support regions are formed from at least two subassemblies and the collar is essentially planar before installation on a victim and wherein the neck region includes a provision for adjusting a cervical collar for the length of a victim's neck after the cervical collar is placed upon the victim, by adjusting the vertical height of the neck support region.

4. The adjustment provision of claim 3 wherein the vertical adjustment is two sided, allowing independent adjustment of the height of opposite sides of the neck support region, such that either side may be offset in vertical height relative to the other.

* * * * *